(12) United States Patent
Park et al.

(10) Patent No.: US 9,919,997 B2
(45) Date of Patent: Mar. 20, 2018

(54) ONE-POT WATER-FREE IONIC LIQUIDS SYNTHESIS USING TRIALKYL ORTHOESTERS

(71) Applicant: PUSAN NATIONAL UNIVERSITY INDUSTRY UNIVERSITY COOPERATION FOUNDATION OF PUSAN, Busan (KR)

(72) Inventors: Jin Kyoon Park, Busan (KR); Do Joong Kim, Busan (KR); Kyung Hwan Oh, Busan (KR)

(73) Assignee: Pusan National University Industry University Cooperation Foundation of Pusan, Busan (KR)

( * ) Notice: Subject to any disclaimer, the term of this patent is extended or adjusted under 35 U.S.C. 154(b) by 0 days.

(21) Appl. No.: 15/108,737

(22) PCT Filed: Nov. 27, 2014

(86) PCT No.: PCT/KR2014/011509
§ 371 (c)(1),
(2) Date: Jun. 28, 2016

(87) PCT Pub. No.: WO2015/102234
PCT Pub. Date: Jul. 9, 2015

(65) Prior Publication Data
US 2016/0326095 A1    Nov. 10, 2016

(30) Foreign Application Priority Data
Dec. 30, 2013  (KR) .................. 10-2013-0167300

(51) Int. Cl.
| | | |
|---|---|---|
| *C07D 233/58* | (2006.01) | |
| *C07D 217/10* | (2006.01) | |
| *C07D 233/06* | (2006.01) | |
| *C07D 471/04* | (2006.01) | |
| *C07D 207/04* | (2006.01) | |
| *C07D 277/22* | (2006.01) | |
| *C07D 277/62* | (2006.01) | |
| *C07D 207/06* | (2006.01) | |
| *C07D 277/64* | (2006.01) | |
| *C07C 211/63* | (2006.01) | |
| *C07C 53/18* | (2006.01) | |
| *C07C 309/06* | (2006.01) | |
| *C07C 309/30* | (2006.01) | |
| *C07C 311/48* | (2006.01) | |
| *C09K 3/00* | (2006.01) | |

(52) U.S. Cl.
CPC ............ *C07C 211/63* (2013.01); *C07C 53/18* (2013.01); *C07C 309/06* (2013.01); *C07C 309/30* (2013.01); *C07C 311/48* (2013.01); *C07D 207/04* (2013.01); *C07D 207/06* (2013.01); *C07D 217/10* (2013.01); *C07D 233/06* (2013.01); *C07D 233/58* (2013.01); *C07D 277/22* (2013.01); *C07D 277/62* (2013.01); *C07D 277/64* (2013.01); *C07D 471/04* (2013.01); *C09K 3/00* (2013.01)

(58) Field of Classification Search
None
See application file for complete search history.

(56) References Cited

U.S. PATENT DOCUMENTS

2011/0053034 A1    3/2011  Mitsui et al. ................. 429/477

FOREIGN PATENT DOCUMENTS

| JP | 2012-072130 | 4/2012 |
|---|---|---|
| KR | 10-2005-0034794 | 4/2005 |
| WO | WO 00/72956 | 12/2000 |

OTHER PUBLICATIONS

Saravanakumar, Shanmuganathan. Influence of anellation in N-heterocyclic carbenes: Novel quinoxaline-anellated NHCs trapped as transition metal complexes. Chem. Commun. 2006, 640-642.*
Kilincarslan, Rafet. In situ Preparation of Rhodium/N-Heterocyclic Carbene Complexes and use for Addition of Arylboronic Acids to Aldehydes. Journal of Heterocyclic Chemistry. 44(1), (2007) 69-73.*
Ullah, Farman. Stabilization of Unsymmetrically Annelated Imidazol-2-ylidenes with Respect to Their Higher Group 14 Homologues by n-/p-HOMO Inversion. Angew. Chem. Int. Ed. 46, (2007), 2697-2700.*
International Search Report and Written Opinion issued in PCT/KR2014/011509, dated Mar. 5, 2015.
Yoshino et al., "Efficient esterification of carboxylic acids and phosphonic acids with trialkyl orthoacetate in ionic liquid", *Tetrahedron*, 62: 1309-1317, 2006.

* cited by examiner

*Primary Examiner* — Samantha L Shterengarts
(74) *Attorney, Agent, or Firm* — Norton Rose Fulbright US LLP

(57) ABSTRACT

The present disclosure provides a method for producing an ionic liquid, the method comprising: reacting a nitrogen-containing heterocyclic compound or an amine-based compound with an ammonium salt along with trialkyl orthoformate to acquire an alkylated nitrogen-containing heterocyclic compound or an alkylated nitrogen-containing amine-based compound, wherein the alkylated nitrogen-containing heterocyclic compound or the alkylated nitrogen-containing amine-based compound as a cation of the ionic liquid is ionically bonded to an anion included in the ammonium salt to form the ionic liquid.

9 Claims, No Drawings

ONE-POT WATER-FREE IONIC LIQUIDS SYNTHESIS USING TRIALKYL ORTHOESTERS

CROSS-REFERENCE TO RELATED APPLICATIONS

This application is a national phase application under 35 U.S.C. § 371 of International Application No. PCT/KR2014/011509 filed 27 Nov. 2014, which claims priority to Korean Patent Application No. 10-2013-0167300 filed 30 Dec. 2013. The entire contents of each of the above-referenced disclosures is specifically incorporated herein by reference.

BACKGROUND

Field of the Present Disclosure

The present disclosure relates to ionic liquids and a method for producing the same. More particularly, the present disclosure relates to a method for synthesizing various ionic liquids in a one-pot water-free manner using a novel alkylating agent and to the various ionic liquids produced by the method.

Discussion of the Related Art

Recently, room temperature ionic liquids (RTILs) have get great attentions due to their special properties. For example, RTILs may have good solvent properties, thermal and chemical stabilities, high conductivities, and recycling as eco-friendly solvents.

Since the article [Wilkes et al.] disclosed a melt imidazolium salt stable against an air and water, weakly-coordinated anions such as $BF_4^-$, $PF_6^-$, $(CF_3SO_2)_2N^-$ have received attentions due to their low melting points and great thermal stabilities.

The conventional synthesis method for producing the room temperature ionic liquids may include an alkyl halide salt formation, an anion exchange, and a metal halide removal. For this, a reference is made to a following reaction formula (1). In another previous method, a one-pot synthesis of non-coordinated anion RTILs may involve use of a trialkyloxonium $BF_4$ or $PF_4$ salt and N-methyl-bis((trifluoromethyl)sulfonyl)imide. For this, a reference is made to a following reaction formula (2):

The above two methods may be limited to methylation or ethylation of the imidazole. However, a one-pot method for producing both coordinated and non-coordinated anion RTILs by via alkylation has not been disclosed up to now.

A trialkyl orthoformate is volatile and is known to be used for O-alkylation and S-alkylation, heterocyclic synthesis, acetylation of ketone, orthoester alkylation of enolate, formylation and alkylation of aromatic amine under a presence of an acid, and synthesis of a N-heterocyclic carbine (NHC) precursor.

SUMMARY

The present applicants have discovered that as a new property of trialkyl orthoformate compounds, the trialkyl orthoformate compounds may be simply be alkylated under a presence of ammonium salts or Brønsted acids. Based on the new discovery, the present applicants have produced various ionic liquids using the trialkyl orthoester in a one-pot water-free manner.

The present disclosure provides a novel method for producing various ionic liquids in a one-pot manner and without water or without a separate dehydration if water used.

In one aspect, the present disclosure provides a method for producing an ionic liquid, the method comprising: reacting a nitrogen-containing heterocyclic compound or an amine-based compound with an ammonium salt along with trialkyl orthoformate to acquire an alkylated nitrogen-containing heterocyclic compound or an alkylated nitrogen-containing amine-based compound, wherein the alkylated nitrogen-containing heterocyclic compound or the alkylated nitrogen-containing amine-based compound defining a cation of the ionic liquid is ionically bonded to the ammonium salt defining an anion of the ionic liquid.

In one embodiment, the nitrogen-containing heterocyclic compound is one selected from a group consisting of imidazole-based, pyridine-based, pyrrolidine-based, triazole-based, oxazole-based, pyrazole-based, and isoquinoline-based heterocyclic compounds.

In one embodiment, the nitrogen-containing heterocyclic compound is represented by a following formula 1, and the ionic liquid is represented by a following formula 2:

Previous methods

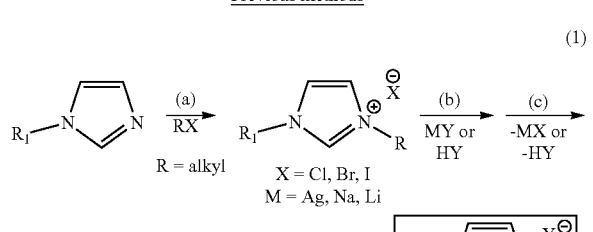

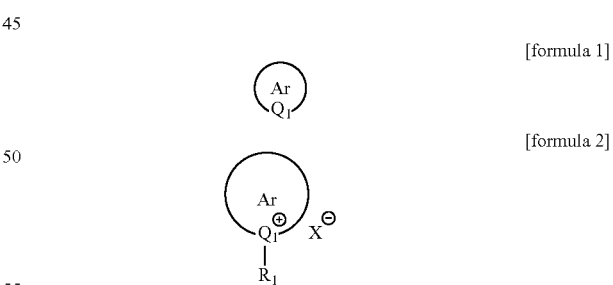

where Ar indicates a heteroaryl ring or a heterocyclic ring having a number of carbons 3 to 10, $Q_1$ indicating $—N=$ or $—NR_2—$, $R_1$ indicates an alkyl group, $R_2$ indicates a hydrogen, alkyl group, allyl group, vinyl group or aryl group, X indicates Cl, Br, I, $BF_4$, $PF_6$, $SbF_6$, bis (trifluoromethyl) sufonylimide, trifluoromethanesulfonate, toluenesulfonate or $NO_3$, and at least one hydrogen atom of Ar is independently substitutable with an alkyl group or ester group.

In one embodiment, the compound represented by the formula 1 is one selected from a group consisting of compounds represented by following formulae 3 to 10 respectively:

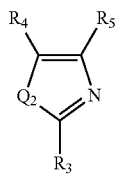
[formula 3]

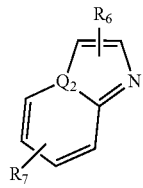
[formula 4]

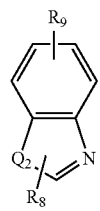
[formula 5]

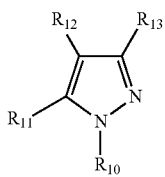
[formula 6]

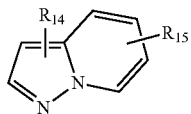
[formula 7]

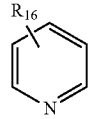
[formula 8]

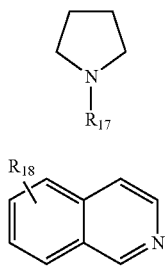
[formula 9]

[formula 10]

where $Q_2$ indicates S, O or $NR_{19}$,
each of $R_3$ to $R_{19}$ independently indicates a hydrogen, alkyl group or aryl group.

In one embodiment, the ammonium salt includes a weakly-coordinated anionic salt compound.

In one embodiment, the ammonium salt contains at least one anion selected from a group consisting anions of Cl, Br, I, $BF_4$, $PF_6$, $SbF_6$, bis(trifluoromethyl)sufonylimide, trifluoromethanesulfonate, toluenesulfonate or $NO_3$.

In one embodiment, the alkylated nitrogen-containing heterocyclic compound is acquired in a water-free and dehydration-free manner.

In one embodiment, the alkylated nitrogen-containing heterocyclic compound is acquired in a one-pot manner.

In one embodiment the amine-based compound is represented by a following formula 11, and the alkylated nitrogen-containing amine-based compound is represented by a following formula 12:

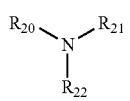
[formula 11]

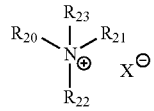
[formula 12]

where, each of $R_{20}$ to $R_{22}$ indicates individually a hydrogen, alkyl group or aryl group, $R_{23}$ indicates an alkyl group, and X indicates Cl, Br, I, $BF_4$, $PF_6$, $SbF_6$, bis (trifluoromethyl) sufonylimide, trifluoromethanesulfonate, toluenesulfonate or $NO_3$.

In one example, when the nitrogen-containing heterocyclic compound is an imidazole compound, a reference may be made to a following reaction formula (3):

New method (3)

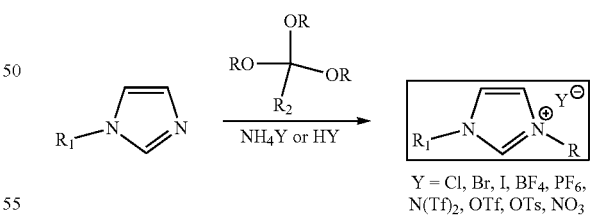

Y = Cl, Br, I, $BF_4$, $PF_6$, $N(Tf)_2$, OTf, OTs, $NO_3$

The byproduct is an alcohol and ester which is removed in a reaction process via evaporation. The possible remaining substance in a reaction solvent reacts with the trialkyl orthoester and thus is removed via evaporation.

In another example, various ionic liquids are produced using a following reaction formula (4). That is, while the nitrogen-containing heterocyclic compound varies, the trialkyl orthoformate varies correspondingly:

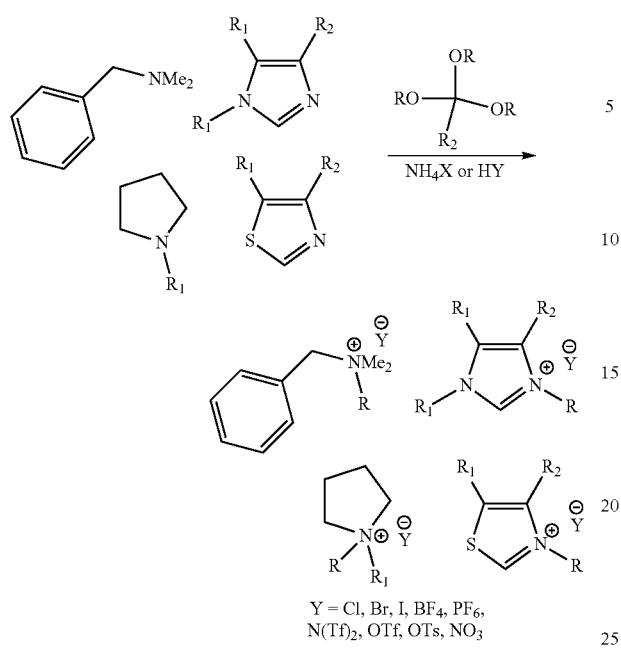

Y = Cl, Br, I, BF$_4$, PF$_6$,
N(Tf)$_2$, OTf, OTs, NO$_3$

DETAILED DESCRIPTIONS

Examples of various embodiments are illustrated and described further below. It will be understood that the description herein is not intended to limit the claims to the specific embodiments described. On the contrary, it is intended to cover alternatives, modifications, and equivalents as may be included within the spirit and scope of the present disclosure as defined by the appended claims.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, s, operations, elements, and/or components, but do not preclude the presence or addition of one or more other features, integers, s, operations, elements, components, and/or portions thereof. As used herein, the term "and/or" includes any and all combinations of one or more of the associated listed items. Expression such as "at least one of" when preceding a list of elements may modify the entire list of elements and may not modify the individual elements of the list.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In the following description, numerous specific details are set forth in order to provide a thorough understanding of the present disclosure. The present disclosure may be practiced without some or all of these specific details. In other instances, well-known process structures and/or processes have not been described in detail in order not to unnecessarily obscure the present disclosure.

As used herein, the term "substantially," "about," and similar terms are used as terms of approximation and not as terms of degree, and are intended to account for the inherent deviations in measured or calculated values that would be recognized by those of ordinary skill in the art. Further, the use of "may" when describing embodiments of the present disclosure refers to "one or more embodiments of the present disclosure."

Productions of Ionic Liquids 1 to 12 and NMR Analysis Results-1
Ionic Liquid 1

1-buytl-3-methylimidazolium hexafluorophosphate

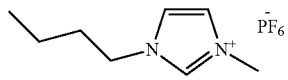

1-buytlimidazole 1.82 mmol (0.24 mL) and NH$_4$PF$_6$ 2.18 mmol (365 mg) and trimethyl orthoformate 9.1 mmol (1 mL) are input into a Schlenk tube, and then are subjected to a reflux reaction under a presence of air or N$_2$. After confirming that protonated imidazole is removed, remaining trimethyl orthoformate is removed in a vacuum. Then, the resulting product is dissolved in ethyl acetate and a small amount of methanol and in turn is passed through a basic alumina to deprotonate a small amount of protonated imidazole. The solvent is removed from the passed-through solution via evaporation in a vacuum and then the final product is subjected to a NMR (nuclear magnetic resonance) analysis. Yield: 95%.

$^1$H NMR δ0.90 (t, J=7.5 Hz, 3H) 1.28 (sextet, J=7.5 Hz, 2H) 1.77 (quintet, J=7.5 Hz, 2H) 3.84 (s, 3H) 4.15 (d, J=7.5 Hz, 2H) 7.65 (s, 1H) 7.71 (s, 1H) 9.05 (s, 1H)
$^{13}$C NMR δ13.80 19.40 31.97 36.28 49.20 122.83 124.19 137.12

Ionic Liquid 2

1-buytl-3-methylimidazolium tetrafluoroborate

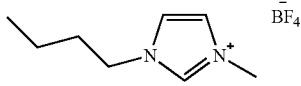

1-buytlimidazole 1.82 mmol (0.24 mL) and NH$_4$BF$_4$ 2.18 mmol (229 mg) and trimethyl orthoformate 9.1 mmol (1 mL) are input into the Schlenk tube and then are subjected to a reflux reaction under a presence of air or N$_2$. After confirming that protonated imidazole is removed, remaining trimethyl orthoformate is removed in a vacuum. Then, the resulting product is dissolved in ethyl acetate and a small amount of methanol and in turn is passed through a basic alumina to deprotonate a small amount of protonated imidazole. The solvent is removed from the passed-through solution via evaporation in a vacuum and then the final product is subjected to a NMR (nuclear magnetic resonance) analysis. Yield: 98%.

¹H NMR δ0.89 (t, J=7.5 Hz, 3H) 1.24 (sextet, J=7.5 Hz, 2H) 1.76 (quintet, J=7.5 Hz, 2H) 3.84 (s, 3H) 4.16 (d, J=7.5 Hz, 2H) 7.65 (s, 1H) 7.72 (s, 1H) 9.02 (s, 1H)
¹³C NMR δ13.83 19.40 31.99 36.29 49.18 122.86 124.19 137.10

Ionic Liquid 3

1-buytl-3-methylimidazolium bromide

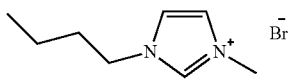

1-buytlimidazole 1.82 mmol (0.24 mL) and NH₄Br 2.18 mmol (214 mg) and trimethyl orthoformate 9.1 mmol (1 mL) are input into the Schlenk tube and then are subjected to a reflux reaction under a presence of air or N₂. After confirming that protonated imidazole is removed, remaining trimethyl orthoformate is removed in a vacuum. Then, the resulting product is dissolved in ethyl acetate and in turn is passed through a basic alumina to deprotonate a small amount of protonated imidazole. The solvent is removed from the passed-through solution via evaporation in a vacuum and then the final product is subjected to a NMR (nuclear magnetic resonance) analysis. Yield: 95%.

¹H NMR δ0.89 (t, J=7.5 Hz, 3H) 1.22 (sextet, J=7.5 Hz, 2H) 1.74 (quintet, J=7.5 Hz. 2H) 3.88 (s, 3H) 4.21 (t, J=7.5 Hz, 2H) 7.82 (s, 1H) 7.91 (s, 1H) 9.45 (s, 1H)
¹³C NMR δ13.94 19.40 32.08 36.49 49.09 122.92 124.16 137.21

Ionic Liquid 4

1-buytl-3-methylimidazolium nitrate

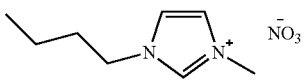

1-buytlimidazole 1.82 mmol (0.24 mL) and NH₄NO₃ 2.18 mmol (175 mg) and trimethyl orthoformate 9.1 mmol (1 mL) are input into the Schlenk tube and then are subjected to a reflux reaction under a presence of air or N₂. After confirming that protonated imidazole is removed, remaining trimethyl orthoformate is removed in a vacuum. Then, the resulting product is dissolved in ethyl acetate and a small amount of methanol and in turn is passed through a basic alumina to deprotonate a small amount of protonated imidazole. The solvent is removed from the passed-through solution via evaporation in a vacuum and then the final product is subjected to a NMR (nuclear magnetic resonance) analysis. Yield: 94%.

¹H NMR δ0.86 (t, J=7.5 Hz, 3H) 1.21 (sextet, J=7.5 Hz, 2H) 1.74 (quintet, J=7.5 Hz. 2H) 3.85 (s, 3H) 4.17 (t, J=7.5 Hz, 2H) 7.72 (s, 1H) 7.80 (s, 1H) 9.24 (s, 1H)
¹³C NMR δ13.85 19.43 32.05 36.27 49.15 122.95 124.25 137.37

Ionic Liquid 5

1-buytl-3-methylimidazolium iodide

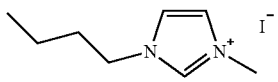

1-buytlimidazole 1.82 mmol (0.24 mL) and NH₄I 2.18 mmol (317 mg) and trimethyl orthoformate 9.1 mmol (1 mL) are input into the Schlenk tube and then are subjected to a reflux reaction under a presence of air or N₂. After confirming that protonated imidazole is removed, remaining trimethyl orthoformate is removed in a vacuum. Then, the resulting product is dissolved in ethyl acetate and a small amount of methanol and in turn is passed through a basic alumina to deprotonate a small amount of protonated imidazole. The solvent is removed from the passed-through solution via evaporation in a vacuum and then the final product is subjected to a NMR (nuclear magnetic resonance) analysis. Yield: 98%.

¹H NMR δ0.88 (t, J=7.5 Hz, 3H) 1.23 (sextet, J=7.5 Hz, 2H) 1.74 (quintet, J=7.5 Hz. 2H) 3.85 (s, 3H) 4.17 (t, J=7.5 Hz, 2H) 7.71 (s, 1H) 7.78 (s, 1H) 9.13 (s, 1H)

Ionic Liquid 6

1-buytl-3-methylimidazolium

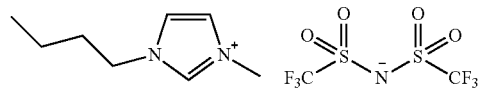

1-buytlimidazole 1.28 mmol (0.168 mL) and bis (trifluoromethane) sulfonimide 1.28 mmol (360 mg) are input and stirred for 30 min in the Schlenk tube. Then, the resultant product reflux-reacts with trimethyl orthoformate 9.1 mmol (0.7 mL) under a presence of N₂. After confirming that protonated imidazole is removed, remaining trimethyl orthoformate is removed in a vacuum. Then, the resulting product is dissolved in ethyl acetate and a small amount of methanol and in turn is passed through a basic alumina to deprotonate a small amount of protonated imidazole. The solvent is removed from the passed-through solution via evaporation in a vacuum and then the final product is subjected to a NMR (nuclear magnetic resonance) analysis. Yield: 95%.

¹H NMR δ0.89 (t, J=7.5 Hz, 3H) 1.24 (sextet, J=7.5, 2H) 1.76 (quintet, J=7.5 Hz. 2H) 3.84 (s, 3H) 4.15 (t, J=7.5 Hz, 2H) 7.68 (s, 1H) 7.75 (s, 1H) 9.08 (s, 1H)
¹³C NMR 13.69 19.38 31.99 36.30 49.23 113.78 118.78 122.31 122.87 124.22 126.57 137.17

Ionic Liquid 7

1,3-dimethylimidazolium hexafluorophosphate

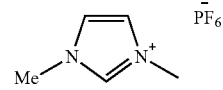

1-methylimidazole 1.82 mmol (0.145 mL) and NH₄PF₆ 2.18 mmol (365 mg) and trimethyl orthoformate 9.1 mmol (1 mL) are input into the Schlenk tube and then are subjected to a reflux reaction under a presence of air or N₂. After confirming that protonated imidazole is removed, remaining trimethyl orthoformate is removed in a vacuum. Then, the resulting product is dissolved in ethyl acetate and a small amount of methanol and in turn is passed through a basic alumina to deprotonate a small amount of protonated imidazole. The solvent is removed from the passed-through solution via evaporation in a vacuum and then the final product is subjected to a NMR (nuclear magnetic resonance) analysis. Yield: 97%.

$^1$H NMR δ3.84 (s, 6H) 7.64 (s, 2H) 8.99 (s, 1H)

$^{13}$C NMR δ36.28 124.08 137.69

Ionic Liquid 8

1-vinyl-3-methylimidazolium hexafluorophosphate

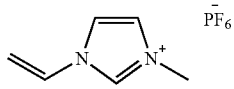

1-vinylimidazole 1.82 mmol (0.164 mL) and NH$_4$PF$_6$ 2.18 mmol (365 mg) and trimethyl orthoformate 9.1 mmol (1 mL) are input into the Schlenk tube and then are subjected to a reflux reaction under a presence of air or N$_2$. After confirming that protonated imidazole is removed, remaining trimethyl orthoformate is removed in a vacuum. Then, the resulting product is dissolved in ethyl acetate and a small amount of methanol and in turn is passed through a basic alumina to deprotonate a small amount of protonated imidazole. The solvent is removed from the passed-through solution via evaporation in a vacuum and then the final product is subjected to a NMR (nuclear magnetic resonance) analysis. Yield: 98%.

$^1$H NMR δ3.88 (s, 3H) 3.39 (d, J=8.8 Hz, 1H) 5.90 (d, J=15.7 Hz, 1H) 7.26 (dd, J1=15.7 Hz, J2=8.8 Hz) 7.82 (s, 1H) 8.15 (s, 1H) 9.44 (s, 1H)

$^{13}$C NMR δ36.57 109.10 119.51 124.97 129.409 136.65

Ionic Liquid 9

1-allyl-3-methylimidazolium hexafluorophosphate

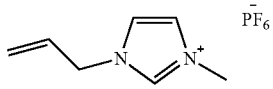

1-allylimidazole 1.82 mmol (0.194 mL) and NH$_4$PF$_6$ 2.18 mmol (365 mg) and trimethyl orthoformate 9.1 mmol (1 mL) are input into the Schlenk tube and then are subjected to a reflux reaction under a presence of air or N$_2$. After confirming that protonated imidazole is removed, remaining trimethyl orthoformate is removed in a vacuum. Then, the resulting product is dissolved in ethyl acetate and a small amount of methanol and in turn is passed through a basic alumina to deprotonate a small amount of protonated imidazole. The solvent is removed from the passed-through solution via evaporation in a vacuum and then the final product is subjected to a NMR (nuclear magnetic resonance) analysis. Yield: 98%.

$^1$H NMR δ3.86 (s, 3H) 4.83 (d, J=6 Hz, 2H) 5.28 (d, J=17, 1H) 5.39 (d, J=11.5, 1H) 7.66 (s, 2H) 9.06 (s, 1H)

$^{13}$C NMR δ36.38 51.48 120.91 122.93 124.38 132.19 137.27

Ionic Liquid 10

1-benzyl-3-methylimidazolium hexafluorophosphate

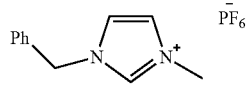

1-benzylimidazole 1.82 mmol (288 mg) and NH$_4$PF$_6$ 2.18 mmol (365 mg) and trimethyl orthoformate 9.1 mmol (1 mL) are input into the Schlenk tube and then are subjected to a reflux reaction under a presence of air or N$_2$. After confirming that protonated imidazole is removed, remaining trimethyl orthoformate is removed in a vacuum. Then, the resulting product is dissolved in ethyl acetate and a small amount of methanol and in turn is passed through a basic alumina to deprotonate a small amount of protonated imidazole. The solvent is removed from the passed-through solution via evaporation in a vacuum and then the final product is subjected to a NMR (nuclear magnetic resonance) analysis. Yield: 93%.

$^1$H NMR δ3.83 (s, 3H) 5.39 (s, 2H) 7.40 (s, 5H) 7.67 (s, 1H) 7.75 (s, 1H) 9.17 (s, 1H)

$^{13}$C NMR δ36.53 25.60 123.03 124.68 128.93 129.42 129.67 135.48 137.35

Ionic Liquid 11

1-phenyl-3-methylimidazolium hexafluorophosphate

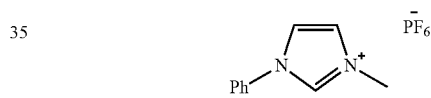

1-phenylimidazole 1.82 mmol (0.23 mL) and NH$_4$PF$_6$ 2.18 mmol (365 mg) and trimethyl orthoformate 9.1 mmol (1 mL) are input into the Schlenk tube and then are subjected to a reflux reaction under a presence of air or N$_2$. After confirming that protonated imidazole is removed, remaining trimethyl orthoformate is removed in a vacuum. Then, the resulting product is dissolved in ethyl acetate and a small amount of methanol and in turn is passed through a basic alumina to deprotonate a small amount of protonated imidazole. The solvent is removed from the passed-through solution via evaporation in a vacuum and then the final product is subjected to a NMR (nuclear magnetic resonance) analysis. Yield: 91%.

$^1$H NMR δ3.94 (s, 1H) 7.59 (d, J=7.2 Hz, 1H) 7.65 (t, J=7.2 Hz, 2H) 7.80 (d, J=7.2 Hz, 2H) 7.95 (s, 1H) 8.29 (s, 1H) 9.74 (s, 1H)

$^{13}$C NMR δ36.80 121.70 122.53

Ionic Liquid 12

1-phenyl-3-isopropylimidazolium hexafluorophosphate

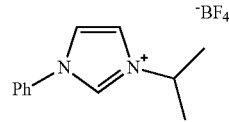

1-phenylimidazole 0.9 mmol (1 eq, 0.24 mL) and NH$_4$BF$_4$ 1.08 mmol (1.2 eq, 115 mg) and triisopropyl orthoformate 4.5 mmol (0.5 mL) are input into the Schlenk tube and then are subjected to a reflux reaction under a presence of air or N$_2$. After confirming that protonated imidazole is removed, remaining triisopropyl orthoformate is removed in a vacuum. Then, the resulting product is dissolved in ethyl acetate and a small amount of methanol and in turn is passed through a basic alumina to deprotonate a small amount of protonated imidazole. The solvent is removed from the passed-through solution via evaporation in a vacuum and then the final product is subjected to a NMR (nuclear magnetic resonance) analysis. Yield: 90%.

$^1$H NMR δ1.55 (d, J=6.9 Hz, 6H) 4.70 (S, J=6.9 Hz, 1H) 7.59 (d, J=7.2 Hz, 1H) 7.65 (t, J=7.2 Hz, 2H) 7.80 (d, J=7.2 Hz, 2H) 8.16 (s, 1H) 8.35 (s, 1H) 9.69 (s, 1H)

$^{13}$C NMR 122.87 53.68 121.99 122.17 122.64 130.40 130.78 134.84 135.55

Productions of Ionic Liquids 13 to 22 and Yields-1

Using 1-buytlimidazole and various acid sources (HX), ionic liquids containing 1-buytl-3-methylimidazolium are produced via a below reaction formula (5). This is indicated in a below table 1. The 1-buytlimidazole and acid sources are mixed with each other at 0° C., and, then, water is removed from the mixture using phosphorus pentoxide in a lowered pressure state. In turn, trimethyl orthoformate is added to and reacted with the resultant product for a given time period. Then, remaining trimethyl orthoformate is removed to acquire each of the ionic liquids 13 to 22. For productions of the ionic liquids 13 to 22, the acid sources, reaction temperatures, reaction durations and yields of the ionic liquids are indicated from the below table 1:

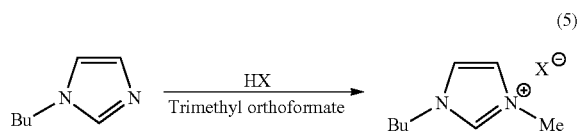

(5)

TABLE 1

| acid ionic sources liquid (HX) | reaction temperatures | reaction durations | ionic liquids [BMIM][X] | yield$^a$ |
|---|---|---|---|---|
| 13 NH$_4$Cl | 110° C. | 24 hours | [BMIM][Cl] | 50% |
| 14 NH$_4$Br | 110° C. | 22 hours | [BMIM][Br] | 96% |
| 15 NH$_4$I | 110° C. | 20 hours | [BMIM][I] | 97% |
| 16 NH$_4$NO$_3$ | 110° C. | 48 hours | [BMIM][NO$_3$] | 96% |
| 17 NH$_4$BF$_4$ | 110° C. | 17 hours | [BMIM][BF$_4$] | 97% |
| 18 NH$_4$PF$_6$ | 110° C. | 17 hours | [BMIM][PF$_6$] | 88% |
| 19 HBF$_4$ | 110° C. | 20 hours | [BMIM][BF$_4$] | 96% |
| 20 HPF$_6$ | 110° C. | 20 hours | [BMIM][PF$_6$] | 95% |
| 21 HN(Tf)$_2$ | 110° C. | 20 hours | [BMIM][N(Tf)$_2$] | 99% |
| 22 CF$_3$SO$_3$H | 110° C. | 20 hours | [BMIM][CF$_3$COO] | 95% |
| 23 p-TsOH | 110° C. | 20 hours | [BMIM][OTs] | 94% |

$^a$yield is measured by $^1$H NMR.

In the above table 1, "Bu" represents a buytl group, and "Me" represents a methyl group.

Productions of Ionic Liquids 24 to 33 and Yields-2

Using 1-alkylimidazole and acid sources (HX) and tri-alkyl orthoester, ionic liquids 24 to 33 are produced. Further, using isoquinoline and acid sources and trialkyl orthoester, an ionic liquid 34 is produced. Each production process of the ionic liquids 24 to 34 is substantially the same as that for each of the ionic liquids 13 to 23. However, differences therebetween in terms of acid sources, reaction durations, reaction temperatures and yields are indicated from a following table 2 for the ionic liquids 24 to 34:

TABLE 2

| ionic liquid | Acid sources (HX) | reaction temperatures | reaction durations | ionic liquid formulae | yield$^a$ |
|---|---|---|---|---|---|
| 24 | NH$_4$BF$_4$ | 110° C. | 20 hours | | 94% |
| 25 | NH$_4$BF$_4$ | 110° C. | 22 hours | | 96% |
| 26 | NH$_4$BF$_4$ | 110° C. | 19 hours | | 97% |
| 27 | NH$_4$BF$_4$ | 110° C. | 20 hours | | 96% |
| 28 | NH$_4$BF$_4$ | 110° C. | 22 hours | | 96% |

TABLE 2-continued

| ionic liquid | Acid sources (HX) | reaction temperatures | reaction durations | ionic liquid formulae | yield[a] |
|---|---|---|---|---|---|
| 29 | HBF$_4$ | 120° C. | 25 hours | Bu-N⊕=N-Et BF$_4$⊖ | 91% |
| 30 | HBF$_4$ | 130° C. | 28 hours | Bu-N⊕=N-nPr BF$_4$⊖ | 93% |
| 31 | HBF$_4$ | 130° C. | 24 hours | Bu-N⊕=N-iPr BF$_4$⊖ | 79% |
| 32 | HBF$_4$ | 140° C. | 24 hours | Bu-N⊕=N-Bu BF$_4$⊖ | 94% |
| 33 | NH$_4$BF$_4$ | 110° C. | 24 hours | Ph-N⊕=N-Me BF$_4$⊖ | N.R |
| 34 | NH$_4$BF$_4$ | 110° C. | 24 hours | isoquinolinium-Me BF$_4$⊖ | 89% |

[a] yield is measured by $^1$H NMR

In the above table 2, "Me" represents a methyl group; "Ph" represents a phenyl group; "Bu" represents a buytl group; "Et" represent an ethyl group; "iPr" represents an isopropyl group; and "nPr" represents a n-propyl group.

Productions of Ionic Liquids 35 to 38 and Yields-3

Using imidazole and acid sources (HX) and trialkyl orthoester, ionic liquids 35 to 38 are produced via a blow reaction formula (6). Each production process of the ionic liquids 35 to 38 is substantially the same as that for each of the ionic liquids 13 to 23. However, differences therebetween in terms of acid sources, reaction durations, reaction temperatures and yields are indicated from a following table 3 for the ionic liquids 35 to 38:

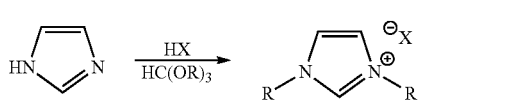
(6)

TABLE 3

| ionic liquid | acid sources (HX) | R | reaction temperatures | reaction durations | yield[a] |
|---|---|---|---|---|---|
| 35 | HBF$_4$ | Methyl group | 110° C. | 20 hours | 84% |
| 36 | HBF$_4$ | Ethyl group | 130° C. | 20 hours | 68% |
| 37 | HBF$_4$ | Isopropyl group | 130° C. | 40 hours | 31% |
| 38 | p-TsOH | Ethyl group | 130° C. | 24 hours | 89 |

[a] yield is measured by $^1$H NMR

Productions of Ionic Liquids 39 to 51 and NMR Analysis Results-2

Each of ionic liquids 39 to 51 is produced using each process as will be described later. In this connection, all of these process may involve in a benzoin condensation reaction commonly as follows:

In a flame-dried Schlenk tube with a magnet string bar, 4-chlorobenzaldehyde 0.50 mmol (70.3 mg, 1.0 eq.), indicated thiazolium precatalyst 0.05 mmol (1.0 eq.) and DBU or Et$_3$N 0.10 mmol (0.2 eq.) are dissolved in dry degassed MeOH 2 mL or MeOH/H$_2$O (0.5 mL/1.5 mL). The resultant mixture is agitated in an argon atmosphere to complete the reaction thereof. The solvent is removed from the resultant solution via evaporation in a vacuum. In order to dissolve the thus-left product in CDCl$_3$ (1 mL), dibromomethane 0.25 mmol (0.5 eq.) is added thereto as a standard substance to determine $^1$H NMR yields.

Ionic Liquid 39

3,5-dimethylthiazole-3-ium tetrafluoroborate

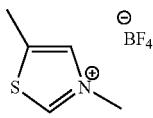

Aqueous tetrafluoroboric acid 1.82 (0.237 mL) is added into 5-methylthiazole (5-methylthiazole) 1.82 mmol (0.16 mL) at 0° C. Then, water is removed from the solution using phosphorus pentoxide in a lowered pressure state. Trimethyl orthoformate 9.1 mmol (1 mL) is added into the resultant product, which is heated to 110° C. and maintained for 24 hours while maintain the 110° C. temperature. Thereafter, trimethyl orthoformate is removed in a lowered pressure state. The thus-left product is dissolved in acetonitrile and the solution is filtered through the basic alumina and is concentrated to acquire 1.73 mmol (347 mg) of 3,5-dimethylthiazole-3-ium tetrafluoroborate as the ionic liquid 39 (yield: 95%). The final product is subjected to NMR.

$^1$H NMR (300 MHz, CDCl$_3$): δ=2.54 (s, 3H) 4.12 (s, 3H) 8.21 (s, 1H) 9.9 (s, 1H)

$^{13}$CNMR (75 MHz, CDCl$_3$): δ=12.42 135.73 139.62 158.42

Ionic Liquid 40

3-isopropyl-5-methylthiazole-3-ium tetrafluoroborate

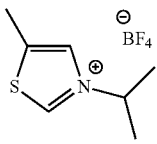

Aqueous tetrafluoroboric acid 1.82 (0.237 mL) is added into 5-methylthiazole (5-methylthiazole) 1.82 mmol (0.16 mL) at 0° C. Then, water is removed from the solution using phosphorus pentoxide in a lowered pressure state. Triisopropyl orthoformate 9.1 mmol (2 mL) is added into the resultant product, which is heated to 130° C. and maintained for 25 hours while maintain the 130° C. temperature. Thereafter, triisopropyl orthoformate is removed in a lowered pressure state. Then, the thus-left product is dissolved in ethyl acetate and methanol. The solution is filtered through the basic alumina and is concentrated to acquire 1.73 mmol (396 mg) of 3-isopropyl-5-methylthiazole-3-ium tetrafluoroborate as the ionic liquid 40 (yield: 94%). The final product is subjected to NMR.

$^1$H NMR (300 MHz, CDCl$_3$): δ=1.55 (d, 3=6.6, Hz, 6H) 2.59 (s, 3H) 4.87 (septet, 3=6.6 Hz, 1H) 8.04 (s, 1H) 10.21 (s, 1H)

$^{13}$CNMR (75 MHz, CDCl$_3$): δ=12.74 22.51 59.00 132.67 140.40 156.41

Ionic Liquid 41

3-buytl-5-methylthiazole-3-ium tetrafluoroborate

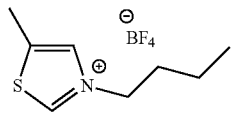

Aqueous tetrafluoroboric acid 1.82 (0.237 mL) is added into 5-methylthiazole (5-methylthiazole) 1.82 mmol (0.16 mL) at 0° C. Then, water is removed from the solution using phosphorus pentoxide in a lowered pressure state. Tribuytl orthoformate 9.1 mmol (2.4 mL) is added into the resultant product, which is heated to 140° C. and maintained for 48 hours while maintain the 140° C. temperature. Thereafter, the tributyl orthoformate is removed in a lowered pressure state. The thus-left product is dissolved in acetonitrile and the solution is filtered through the basic alumina and is concentrated to acquire 3-buytl-5-methylthiazole-3-ium tetrafluoroborate 1.78 mmol (433 mg) as the ionic liquid 41 (yield: 98%). The final product is subjected to NMR.

$^1$H NMR (300 MHz, CDCl$_3$): δ0.90 (t, 3=7.3 Hz, 3H) 1.25 (sextet, 3=7.3 Hz, 2H) 1.82 (quintet, 3=7.3 Hz, 2H) 2.55 (s, 3H) 4.46 (t, 3=7.3 Hz, 2H) 8.34 (s, 1H) 10.00 (s, 1H)

$^{13}$CNMR (75 MHz, CDCl$_3$): δ=12.59 13.69 19.22 31.83 134.58 140.22 157.77

Ionic Liquid 42

3,4-dimethylthiazole-3-ium tetrafluoroborate

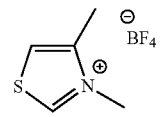

Aqueous tetrafluoroboric acid 1.82 (0.237 mL) is added into 5-methylthiazole (5-methylthiazole) 1.82 mmol (0.16 mL) at 0° C. Then, water is removed from the solution using phosphorus pentoxide in a lowered pressure state. Trimethyl orthoformate 9.1 mmol (1 mL) is added into the resultant product, which is heated to 110° C. and maintained for 23 hours while maintain the 110° C. temperature. Thereafter, the trimethyl orthoformate is removed in a lowered pressure state. The thus-left product is dissolved in methanol and the solution is filtered through the basic alumina and is concentrated to acquire 3,4-dimethylthiazole-3-ium tetrafluoroborate 1.76 mmol (355 mg) as the ionic liquid 42 (yield: 97%). The final product is subjected to NMR.

$^1$H NMR (300 MHz, CDCl$_3$): δ=2.48 (s, 3H) 4.05 (s, 3H) 7.93 (s, 1H) 10.00 (s, 1H)

$^{13}$CNMR (75 MHz, CDCl$_3$): δ=13.03 121.53 146.67 1259.69

Ionic Liquid 43

3,4-dimethylthiazole-3-ium trifluoromethanesulfonate

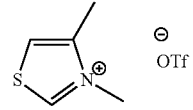

4-methylthiazole 1.82 mmol (0.166 mL) and trifluoromethanesulfonic acid 1.82 mmol (0.159 mL) are mixed with trimethyl orthoformate 9.1 mmol (1 mL). The mixture is heated to 110° C. and maintained for 23 hours for reaction while keeping the 110° C. The trimethyl orthoformate is removed in a lowered pressure state. This crude product is re-crystalized using ethyl acetate and diethyl ether to acquire 3,4-dimethylthiazole-3-ium trifluoromethanesulfonate 1.72 mmol (453 mg) as the ionic liquid 43 (yield 95%). The final product is subjected to NMR.

$^1$H NMR (300 MHz, CDCl$_3$): δ=2.48 (s, 3H) 4.06 (s, 3H) 7.94 (s, 1H) 10.02 (s, 1H)

$^{13}$CNMR (75 MHz, CDCl$_3$): δ=13.06 47.27 114.67 118.94 121.57 123.21 127.48 146.83 159.73

Ionic Liquid 44

3-isopropyl-4-methylthiazole-3-ium tetrafluoroborate

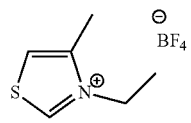

Aqueous tetrafluoroboric acid 1.82 (0.237 mL) is added into 5-methylthiazole 1.82 mmol (0.16 mL) at 0° C. Then, water is removed from the solution using phosphorus pentoxide in a lowered pressure state. Triisopropyl orthoformate 9.1 mmol (2 mL) is added into the resultant product, which is heated to 130° C. and maintained for 25 hours while maintain the 130° C. temperature. Thereafter, the triiopropyl orthoformate is removed in a lowered pressure state. The thus-left product is dissolved in ethyl acetate and methanol and the solution is filtered through the basic alumina and is concentrated to 1.71 mmol (391 mg) of 3-isopropyl-4-methylthiazole-3-ium tetrafluoroborate as the ionic liquid 44 (yield: 94%). The final product is subjected to NMR.

$^1$H NMR (300 MHz, CDCl$_3$): δ=1.54 (d, 3=6.6, Hz 6H) 2.56 (s, 3H) 4.98 (septet, 3=6.6 Hz, 1H) 8.49 (s, 1H) 10.02 (s, 1H)

$^{13}$CNMR (75 MHz, CDCl$_3$): δ=13.28 22.64 55.81 122.14 146.30 157.0

Ionic Liquid 45

3-buytl-4-methylthiazole-3-ium tetrafluoroborate

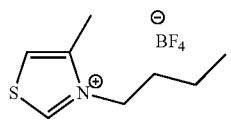

Aqueous tetrafluoroboric acid 1.82 (0.237 mL) is added into 5-methylthiazole 1.82 mmol (0.16 mL) at 0° C. Then, water is removed from the solution using phosphorus pentoxide in a lowered pressure state. Tribuytl orthoformate 9.1 mmol (2.4 mL) is added into the resultant product, which is heated to 140° C. and maintained for 30 hours while maintain the 140° C. temperature. Thereafter, the tributyl orthoformate is removed in a lowered pressure state. The thus-left product is dissolved in acetonitrile and the solution is filtered through the basic alumina and is concentrated to acquire 3-buytl-4-methylthiazole-3-ium tetrafluoroborate 1.76 mmol (429 mg) as the ionic liquid 45 (yield: 97%). The final product is subjected to NMR.

$^1$H NMR (300 MHz, CDCl$_3$): δ=0.92 (t, 3=7.3 Hz, 3H) 1.32 (sextet, 3=7.3 Hz, 2H) 1.79 (quintet, 3=7.3 Hz, 2H) 2.55 (s, 3H) 4.43 (t, 3=7.3 Hz, 2H) 8.01 (s, 1H) 10.10 (s, 1H)

$^{13}$CNMR (75 MHz, CDCl$_3$): δ=13.03 13.77 19.37 31.23 52.55 122.34 146.30 159.40

Ionic Liquid 46

3,4,5-trimethylthiazole-3-ium tetrafluoroborate

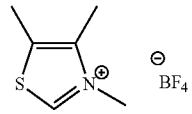

Aqueous tetrafluoroboric acid 1.82 (0.237 mL) is added into 4,5-dimethylthiazole 1.82 mmol (0.19 mL) at 0° C. Then, water is removed from the solution using phosphorus pentoxide in a lowered pressure state. Trimethyl orthoformate 9.1 mmol (1 mL) is added into the resultant product, which is heated to 110° C. and maintained for 24 hours while maintain the 110° C. temperature. Thereafter, the trimethyl orthoformate is removed in a lowered pressure state. This crude product is re-crystalized using ethyl acetate and hexane and, then, the solvent is removed from the solution in a lowered pressure state. Thus, as the ionic liquid 46, 3,4,5-trimethylthiazole-3-ium tetrafluoroborate 1.74 mmol (374 mg) is produced (yield 96%). The final product is subjected to NMR.

$^1$H NMR (300 MHz, CDCl$_3$): δ=2.37 (s, 3H) 2.46 (s, 3H) 4.04 (s, 3H) 9.87 (s, 1H)

$^{13}$CNMR (75 MHz, CDCl$_3$): δ=11.28 12.23 132.77 142.62 156.04

Ionic Liquid 47

3-buytl-4,5-dimethylthiazole-3-ium tetrafluoroborate

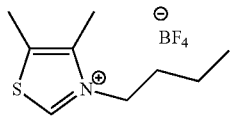

Aqueous tetrafluoroboric acid 1.82 (0.237 mL) is added into 5-methylthiazole 1.82 mmol (0.16 mL) at 0° C. Then, water is removed from the solution using phosphorus pentoxide in a lowered pressure state. Tribuytl orthoformate 9.1 mmol (2.4 mL) is added into the resultant product, which is heated to 140° C. and maintained for 24 hours while maintain the 140° C. temperature. Thereafter, tributyl orthoformate is removed in a lowered pressure state. The thus-left product is dissolved in acetonitrile and the solution is filtered through the basic alumina and is concentrated to acquire 3-buytl-4,5-dimethylthiazole-3-ium tetrafluoroborate 1.76 mmol (452 mg) as the ionic liquid 47 (yield: 97%). The final product is subjected to NMR.

$^1$H NMR (300 MHz, CDCl$_3$): δ=0.93 (t, 3=7.5 Hz, 3H) 1.33 (sextet, 3=7.5 Hz, 2H) 1.78 (quintet, 3=7.5 Hz, 2H) 2.44 (s, 3H) 2.47 (s, 3H) 4.44 (d, 3=7.5 Hz, 2H) 9.56 (s, 1H)

$^{13}$CNMR (75 MHz, CDCl$_3$): δ=11.33 12.34 13.77 19.33 31.20 39.10 53.13 133.57 142.04 155.69

Ionic Liquid 48

3-buytl-4,5-dimethylthiazole-3-ium bis(trifluoromethyl)sulfonylamide

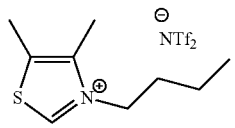

4,5-dimethylthiazole 1.58 mmol (0.166 mL) and bis(trifluoromethane)sulfonimide 1.58 mmol (448 mg) are mixed with tribuytl orthoformate 7.9 mmol (2.1 mL). The mixture is heated to 140° C. and is reacted for 48 hours while keeping the 140° C. The tribuytl orthoformate is removed in a lowered pressure state. Then, the thus-left product is dissolved in a mixture of ethyl acetate and methanol and then the solution is filtered out via the basic alumna and is concentrated to acquire 1.53 mmol (690 mg) of 3-buytl-4,5-dimethylthiazole-3-ium bis(trifluoromethyl)sulfonylamide as the ionic liquid 48 (yield: 97%). The final product is subjected to NMR.

$^1$H NMR (300 MHz, CDCl$_3$): δ=0.88 (t, 3=7.5 Hz, 3H) 1.30 (sextet, 3=7.5 Hz, 2H) 1.75 (quintet, 3=7.3 Hz, 2H) 2.41 (s, 3H) 2.47 (s, 3H) 4.42 (d, 3=7.5 Hz, 2H) 9.56 (s, 1H)

$^{13}$CNMR (75 MHz, CDCl$_3$): δ=11.28 12.30 19.31 31.21 53.15 113.52 117.78 122.05 126.31 133.55 142.03 155.70

Ionic Liquid 49

3-methylbenzo[d]thiazole-3-ium trifluoromethanesulfonate

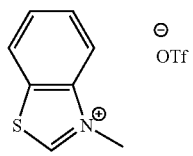

Benzothiazole 1.82 mmol (0.198 mL) and trifluoromethanesulfonic acid 1.82 mmol (0.159 mL) are mixed with trimethyl orthoformate 9.1 mmol (1 mL). The mixture is heated to 110° C. and is reacted for 24 hours while keeping the 110° C. The trimethyl orthoformate is removed in a lowered pressure state. Then, the crude product is re-crystalized using a mixture of ethyl acetate and diethyl ether to acquire 1.72 mmol (516 mg) of 3-methylbenzo[d]thiazole-3-ium trifluoromethanesulfonate as the ionic liquid 49 (yield 96%). The final product is subjected to NMR.

$^1$H NMR (300 MHz, CDCl$_3$): δ=4.40 (s, 3H) 7.85 (t, 3=7.5 Hz, 1H) 7.94 (t, 3=7.5 Hz, 1H) 8.31 (d, 3=7.5 Hz, 1H) 8.49 (d, 3=7.5 Hz, 1H) 10.51 (s, 1H)

$^{13}$CNMR (75 MHz, CDCl$_3$): δ=114.78 117.55 118.97 123.25 125.41 128.82 129.91 131.61 141.46 165.36

Ionic Liquid 50

3-Methylbenzo[d]Thiazole-3-Ium Bis((trifluoromethyl)sulfonyl)amide

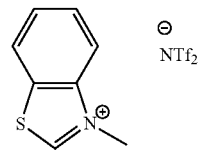

Benzothiazole 1.35 mmol (0.147 mL) and bis(trifluoromethane)sulfonimide 1.34 mmol (378 mg) are mixed with trimethyl orthoformate 9.1 mmol (1 mL). The mixture is heated to 110° C. and is reacted for 24 hours while keeping the 110° C. The trimethyl orthoformate is removed in a lowered pressure state. Then, the crude product is re-crystalized using a mixture of ethyl acetate and diethyl ether to acquire 1.29 mmol (558 mg) of 3-methylbenzo[d]thiazole-3-ium bis((trifluoromethyl)sulfonyl)amide as the ionic liquid 50 (yield 96%). The final product is subjected to NMR.

$^1$H NMR (300 MHz, CDCl$_3$): δ=4.40 (s, 3H) 7.88 (t, 3=7.5 Hz, 1H) 7.94 (t, 3=7.5 Hz, 1H) 8.31 (d, 3=7.5 Hz, 1H) 8.49 (d, 3=7.5 Hz, 1H) 10.52 (s, 1H)

$^{13}$CNMR (75 MHz, CDCl$_3$): δ=113.51 117.53 117.77 122.04 125.39 126.30 128.79 129.87 131.61 141.46 165.36

Ionic Liquid 51

3-isopropylbenzo[d]thiazole-3-ium bis((trifluoromethyl)sulfonyl)amide

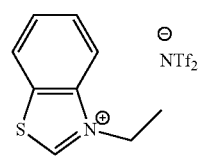

Benzothiazole 2.02 mmol (0.22 mL) and bis(trifluoromethane)sulfonimide 2.02 mmol (568 mg) are mixed with triisopropyl orthoformate 9.1 mmol (2.2 mL). The mixture is heated to 130° C. and is reacted for 26 hours while keeping the 130° C. The triisopropyl orthoformate is removed in a lowered pressure state. Then, the crude product is re-crystalized using a mixture of ethyl acetate and diethyl ether to acquire 1.87 mmol (861 mg) of 3-isopropylbenzo[d]thiazole-3-ium bis((trifluoromethyl)sulfonyl)amide as the ionic liquid 51 (yield 93%). The final product is subjected to NMR.

$^1$H NMR (300 MHz, CDCl$_3$): δ=1.70 (d, 3=6.6 Hz 6H) 5.44 (septet, 3=6.6 Hz, 1H) 7.87 (t, 3=7.5 Hz, 1H) 7.96 (t, 3=7.5 Hz, 1H) 8.48 (d, 3=7.5 Hz, 1H) 8.53 (d, 3=7.5 Hz, 1H) 10.60 (s, 1H)

$^{13}$CNMR (75 MHz, CDCl$_3$): δ=21.79 56.39 113.50 117.80 122.03 125.76 126.30 129.04 130.07 132.04 140.48 162.57

Productions of Ionic Liquids 52 to 56 and NMR Analysis Results-3

Ionic Liquid 52

3-(ethoxycarboxyl)-1-isopropylpyrazolo[1,5-a]pyridine-1-ium tetrafluoroborate

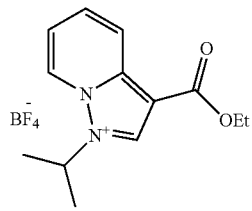 [SMILES: "BF4" ; CCOC(=O)c1c[n+](C(C)C)n2ccccc12]

Ethyl pyrazolo[1,5-a]pyridine-3-carboxylate 0.28 mmol (53 mg, 1 eq) is input in a dropwise manner into HBF$_4$ 48 wt % water solution 0.28 mmol (36 μl, 1 eq.) at 0° C. and the mixture is agitated at a room for 30 mins. Then the water is evaporated from the mixture. Then, triisopropyl orthoformate 1.4 mmol (0.3 mL, 5 eq) is added to the water-free mixture and then is subjected to a reflux reaction under a presence of N$_2$. After it is conformed that protonated pyrazol is removed, remaining triisopropyl orthoformate is removed. The thus-left product is dissolved in a mixture of methylencloride and methanol. The solution is passed through the basic alumina and the solvent is removed from the passed through solution in a vacuum. The final product is subjected to NMR (yield: 95%).

$^1$H NMR (DMSO-d6) δ1.38 (t, 3=7.5 Hz, 3H) 1.63 (d, 3=6.3 Hz, 6H) 4.44 (q, 3=7.5 Hz, 2H) 5.37 (septet, 3=6.3, 1H) 7.84 (t, 3=6.9 Hz, 1H) 8.17 (t, 3=8.0 Hz, 1H) 8.52 (d, 3=9.0 Hz, 1H) 9.50 (d, 3=6.9 Hz, 1H) 9.54 (s, 1H)

Ionic Liquid 53

3-(methoxycarbonyl)-1-methylpyrazolo[1,5-a]pyridine-1-ium tetrafluoroborate

Methyl pyrazolo[1,5-a]pyridine-3-carboxylate 0.32 mmol (53 mg, 1 eq) is input in a dropwise manner into HBF$_4$ 48 wt % water solution 0.32 mmol (41 μl, 1 eq.) at 0° C. and the mixture is agitated at a room for 30 mins. Then the water is evaporated from the mixture. Then, trimethyl orthoformate 1.6 mmol (0.8 mL, 5 eq) is added to the water-free mixture and then is subjected to a reflux reaction under a presence of N$_2$. After it is conformed that protonated pyrazol is removed, remaining trimethyl orthoformate is removed. The thus-left product is dissolved in a mixture of methylencloride and methanol. The solution is passed through the basic alumina and the solvent is removed from the passed through solution in a vacuum. The final product is subjected to NMR (yield: 96%).

$^1$H NMR (DMSO-d6) δ3.93 (s, 3H) 4.30 (s, 3H) 7.84 (t, 3=6.9 Hz, 1H) 8.16 (t, 3=8.0 Hz, 1H) 8.48 (d, 3=9.0 Hz, 1H) 9.30 (d, 3=6.9 Hz, 1H) 9.48 (s, 1H)

Ionic Liquid 54

1-isopropyl-8-methyl-3-phenylimidazole[1,2-a]pyridine-1-ium tetrafluoroborate

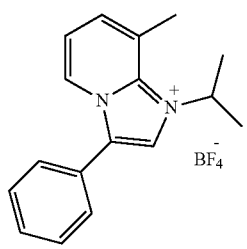

8-methyl-3-phenylimidazo[1,2-a]pyridine 0.48 mmol (100 mg, 1 eq) is input in a dropwise manner into HBF$_4$ 48 wt % water solution 0.48 mmol (62 μl, 1 eq.) at 0° C. and the mixture is agitated at a room for 30 mins. Then the water is evaporated from the mixture. Then, triisopropyl orthoformate 1.6 mmol (0.5 mL, 5 eq) is added to the water-free mixture and then is subjected to a reflux reaction under a presence of N$_2$. After it is conformed that protonated imdazol is removed, remaining triisopropyl orthoformate is removed. The thus-left product is dissolved in methanol. The solution is passed through the basic alumina and the solvent is removed from the passed through solution in a vacuum. The final product is subjected to NMR (yield: 93%).

$^1$H NMR (CDCl$_3$) δ1.68 (d, J=6.3 Hz, 6H) 5.19 (septet, J=6.3, 1H) 7.24 (d, J=7.2 Hz, 1H) 7.59 (s, 5H) 7.79 (s, 1H) 8.02 (s, J=7.2 Hz, 1H) 8.35 (d, 1H)

Ionic Liquid 55

1,1-dimethylpyrrolidinium tetrafluoroborate

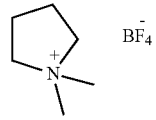

1-methylpyrrolidin 4.80 mmol (0.5 mL, 1 eq) is input in a dropwise manner into HBF$_4$ 48 wt % water solution 4.80 mmol (0.63 mL, 1 eq.) at 0° C. and the mixture is agitated at a room for 30 mins. Then the water is evaporated from the mixture. Then, the prepared 1-methylirolidium tetrafluoroborate 4.7 mmol (410 mg, 1 eq) is input into a vial and trimethyl orthoformate 23.5 mmol (2.5 ml, 5 eq) is input thereto, which is reacted at 130° C. for 3 hours in a microwave reactor. After confirming that protonated 1-methylpyrrolidin is removed, remaining trimethylpropyl orthoformate is removed in a vacuum. The thus-left product is re-crystalized using methylencloride and diethyl ether. The solvent is removed from the solution in a vacuum. The final product is subjected to NMR (yield: 94%).

$^1$H NMR (DMSO-d6) δ2.07 (br, 4H) 3.05 (s, 6H) 3.42 (br, 4H)

Ionic Liquid 56

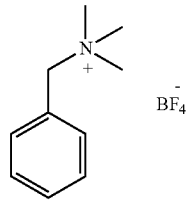

N,N-dimethylbenzylamine 3.64 mmol (0.55 mL, 1 eq) is input in a dropwise manner into HBF$_4$ 48 wt % water solution 3.64 mmol (0.48 mL, 1 eq.) at 0° C. and the mixture is agitated at a room for 30 mins. Then the water is evaporated from the mixture. Then, the prepared N,N-dimethyl-1-phenylmethaneammonium tetrafluoroborate 1.62 mmol (362 mg, 1 eq) is input to a vial and trimethyl orthoformate 8.1 mmol (0.9 ml, 5 eq) in input thereto, which is reacted at 130° C. for 3 hours in a microwave reactor. After confirming that protonated amine is removed, remaining trimethylpropyl orthoformate is removed in a vacuum. The thus-left product is dissolved in acetone and the solution is passed through the basic alumina and the solvent is removed from the solution in a vacuum to acquire a final product, which is subjected to NMR (yield: 97%)

$^1$H NMR (DMSO-d6) δ2.99 (s, 9H) 4.49 (s, 2H) 7.51 (s, 5H)

What is claimed is:

1. A method for producing an ionic liquid, the method comprising:
    reacting a nitrogen-containing heterocyclic compound or an amine-based compound with an ammonium salt along with trialkyl orthoformate to acquire an alkylated nitrogen-containing heterocyclic compound or an alkylated nitrogen-containing amine-based compound,
    wherein the alkylated nitrogen-containing heterocyclic compound or the alkylated nitrogen-containing amine-based compound as a cation of the ionic liquid is ionically bonded to an anion included in the ammonium salt to form the ionic liquid,
    wherein at least one nitrogen atom of the nitrogen-containing heterocyclic compound forms a ring structure before alkylating, and one of the nitrogen atoms included in the ring structure is alkylated to form the cation of the ionic liquid, and
    wherein a nitrogen atom of the amine-based compound is bonded to three functional groups before alkylating, and the nitrogen atom of the amine-based compound is alkylated to form the cation of the ionic liquid without forming a ring structure.

2. The method of claim 1, wherein the nitrogen-containing heterocyclic compound is one selected from a group consisting of imidazole-based, pyridine-based, pyrrolidine-based, triazole-based, oxazole-based, pyrazole-based, and isoquinoline-based heterocyclic compounds.

3. The method of claim 1, wherein the nitrogen-containing heterocyclic compound is represented by a following formula 1, and the ionic liquid is represented by a following formula 2:

[formula 1]

[formula 2]

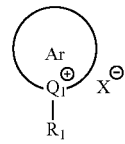

where

Ar indicates a heteroaryl ring or a heterocyclic ring having a number of carbons 3 to 10, $Q_1$ indicating —N= or —NR$_2$—, $R_1$ indicates an alkyl group, $R_2$ indicates a hydrogen, alkyl group, allyl group, vinyl group or aryl group, X indicates Cl, Br, I, BF$_4$, PF$_6$, SbF$_6$, bis (trifluoromethyl) sufonylimide, trifluoromethanesulfonate, toluenesulfonate or NO$_3$, and at least one hydrogen atom of Ar is independently substitutable with an alkyl group or ester group.

4. The method of claim 3, wherein the compound represented by the formula 1 is one selected from a group consisting of compounds represented by following formulae 3 to 10 respectively:

[formula 3]

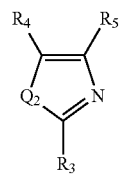

[formula 4]

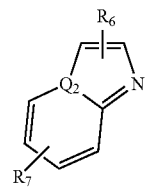

[formula 5]

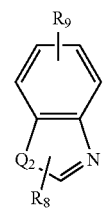

[formula 6]

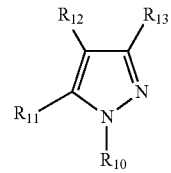

[formula 7]

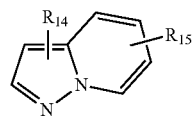

-continued

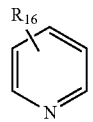 [formula 8]

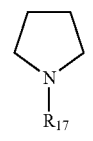 [formula 9]

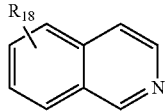 [formula 10]

where, $Q_2$ indicates S, O or $NR_{19}$, each of $R_3$ to $R_{19}$ independently indicates a hydrogen, alkyl group or aryl group.

5. The method of claim 1, wherein the ammonium salt includes a weakly-coordinated anionic salt compound.

6. The method of claim 1, wherein the ammonium salt contains at least one anion selected from a group consisting anions of Cl, Br, I, $BF_4$, $PF_6$, $SbF_6$, bis (trifluoromethyl) sufonylimide, trifluoromethanesulfonate, toluenesulfonate or $NO_3$.

7. The method of claim 1, wherein the alkylated nitrogen-containing heterocyclic compound is acquired in a water-free and dehydration-free manner.

8. The method of claim 1, wherein the alkylated nitrogen-containing heterocyclic compound is acquired in a one-pot manner.

9. The method of claim 1, wherein the amine-based compound is represented by a following formula 11, and the alkylated nitrogen-containing amine-based compound is represented by a following formula 12:

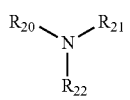 [formula 11]

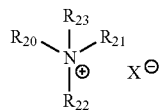 [formula 12]

where each of $R_{20}$ to $R_{22}$ indicates individually a hydrogen, alkyl group or aryl group, $R_{23}$ indicates an alkyl group, and X indicates Cl, Br, I, $BF_4$, $PF_6$, $SbF_6$, bis (trifluoromethyl) sufonylimide, trifluoromethanesulfonate, toluenesulfonate or $NO_3$.

* * * * *